US009588129B2

(12) United States Patent
Stys et al.

(10) Patent No.: US 9,588,129 B2
(45) Date of Patent: *Mar. 7, 2017

(54) METHODS FOR ANALYZING BLOOD TO DETECT DISEASES ASSOCIATED WITH ABNORMAL PROTEIN AGGREGATION

(71) Applicant: Amira Medical Technologies Inc., Calgary (CA)

(72) Inventors: Peter Stys, Calgary (CA); Shigeki Tsutsui, Calgary (CA)

(73) Assignee: Amira Medical Technologies Inc., Calgary, AB (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/833,008

(22) Filed: Mar. 15, 2013

(65) Prior Publication Data
US 2014/0273000 A1  Sep. 18, 2014

(51) Int. Cl.
G01N 33/68 (2006.01)
G06F 19/18 (2011.01)

(52) U.S. Cl.
CPC ......... *G01N 33/6896* (2013.01); *G06F 19/18* (2013.01); *G01N 2333/4709* (2013.01); *G01N 2800/285* (2013.01); *G01N 2800/2814* (2013.01); *G01N 2800/2821* (2013.01); *G01N 2800/2828* (2013.01); *G01N 2800/2835* (2013.01); *G01N 2800/2842* (2013.01)

(58) Field of Classification Search
CPC .............................................. G01N 2800/2821
See application file for complete search history.

(56) References Cited

U.S. PATENT DOCUMENTS

| | | | |
|---|---|---|---|
| 7,713,962 B2 | 5/2010 | Wischik et al. | |
| 7,771,957 B2 | 8/2010 | Fiala | |
| 8,710,193 B2 | 4/2014 | Irie et al. | |
| 2007/0054322 A1 | 3/2007 | Gabizon et al. | |
| 2008/0220449 A1* | 9/2008 | Vasan et al. | 435/7.9 |
| 2008/0268549 A1 | 10/2008 | Nicotera | |
| 2008/0300204 A1 | 12/2008 | Federoff et al. | |
| 2009/0202627 A1* | 8/2009 | Nicolau | 424/450 |
| 2010/0129847 A1 | 5/2010 | Navarrete Santos et al. | |
| 2011/0287473 A1 | 11/2011 | De Barry et al. | |
| 2012/0009685 A1 | 1/2012 | Kim et al. | |
| 2012/0094308 A1 | 4/2012 | Sanchez Ramos | |
| 2012/0172296 A1 | 7/2012 | Tang et al. | |
| 2012/0269738 A1 | 10/2012 | Yang et al. | |
| 2012/0282169 A1 | 11/2012 | Duan et al. | |
| 2012/0302603 A1 | 11/2012 | Yang et al. | |
| 2013/0040319 A1 | 2/2013 | Caughey et al. | |

FOREIGN PATENT DOCUMENTS

| | | |
|---|---|---|
| CA | 2779846 A1 | 5/2011 |
| EP | 1395833 B1 | 3/2004 |
| WO | 9401579 A1 | 1/1994 |
| WO | 9726537 A1 | 7/1997 |
| WO | 2004025295 A2 | 3/2004 |
| WO | 2006020269 A2 | 2/2006 |
| WO | 2010144634 A1 | 12/2010 |
| WO | 2012122236 A2 | 9/2012 |

OTHER PUBLICATIONS

Grathwohl et al. 2009 "formation and maintenance of Alzheimer's disease β-amyloid plaques in the absence of microglia" Nature neuroscience published onlline Oct. 18, 2009 (16 pages).*
Jung et al. 1999 "β-amyloid precursor protein is detectable on monocytes and is increased in Alzheimer's disease" Neurobiol Aging 20:249-257.*
Kremmers et al. 2008 "Quantitative lifetime unmixing of multiexponentially decaying fluorophores using single-frequency fluorescence liftime imaging microscopy" Biophys J 95(1):378-89.*
Apetri 2006 "Secondary structure of .alpha.-synuclein oligomers: characterization by raman and atomic force microscopy" JMB 355:63-71.*
Collins 2004 "Mechanism of prion propogation: amyloid growth occurs by monomer addition" PLoS biology 2(10):1582-1590.*
Mushinka 2007 "fluorescence as a method to reveal structures and membrane-interactions of amyloidogenic proteins" BBA 1768:1862-1885.*
Nilsson 2010 "prion strain interactions are highly selective" J neurosci 30(36):12094-12102.*
Britschgi, M. & Wyss-Coray, T. Systemic and acquired immune responses in Alzheimer's disease. Int Rev Neurobiol 82, 205-233 (2007).
Michaud, J. P. et al. (2013) Real-time in vivo imaging reveals the ability of monocytes to clear vascular amyloid Beta. Cell Rep 5, 646-653.
Nagababu, E., Usatyuk, P. V., Enika, D., Natarajan, V. & Rifkind, J. M. Vascular endothelial barrier dysfunction mediated by amyloid-beta proteins. J Alzheimers Dis 17, 845-854 (2009).
Farkas, I. G. et al. Beta-amyloid peptide-induced blood-brain barrier disruption facilitates T-cell entry into the rat brain. Acta Histochem 105, 115 125 (2003).
Majumdar, A. et al. Degradation of fibrillar forms of Alzheimer's amyloid betapeptide by macrophages. Neurobiol Aging 29, 707-715 (2008).
Simard, A. R., Soulet, D., Gowing, G., Julien, J. P. & Rivest, S. Bone marrowderived microglia play a critical role in restricting senile plaque formation in Alzheimer's disease. Neuron 49, 489-502 (2006).
McKhann, G. M. et al. The diagnosis of dementia due to Alzheimer's disease: recommendations from the National Institute on Aging-Alzheimer's Association workgroups on diagnostic guidelines for Alzheimer's disease. Alzheimers Dement 7, 263-269 (2011).

(Continued)

*Primary Examiner* — Adam M Weidner
(74) *Attorney, Agent, or Firm* — Bereskin & Parr LLP/S.E.N.C.R.L., s.r.l.; I. Laurence MacPhie

(57) ABSTRACT

A method of detecting a disease associated with abnormal protein aggregation in a subject is provided, the method comprising (a) contacting leukocytes from the subject with a probe that binds to pathogenic protein aggregates, and (b) detecting the probe bound to the pathogenic protein aggregates, wherein the presence of pathogenic protein aggregates in the leukocytes is indicative that the subject has a disease associated with abnormal protein aggregation. In one embodiment, the disease is Alzheimer's disease or mild cognitive impairment.

14 Claims, 8 Drawing Sheets

(56) References Cited

OTHER PUBLICATIONS

Figure 1:
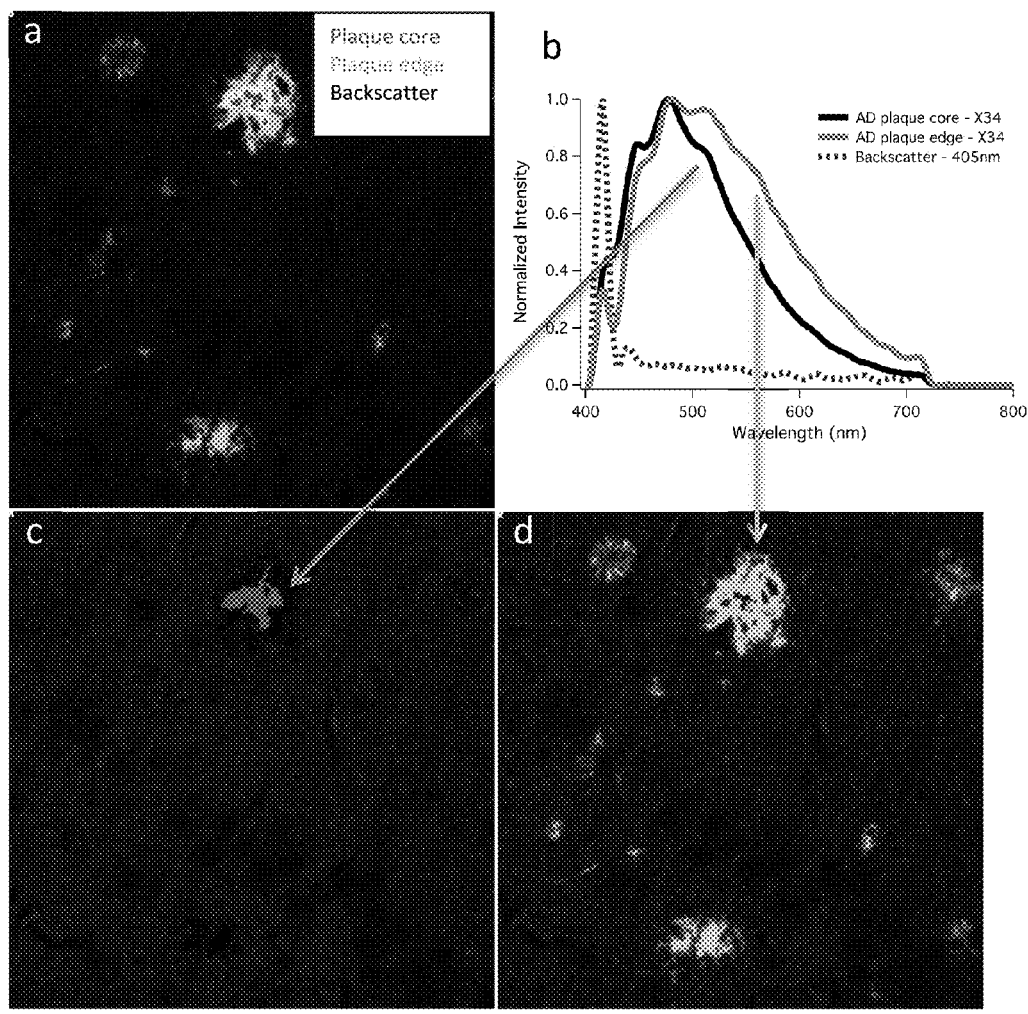

Styren, S. D., Hamilton, R. L., Styren, G. C. & Klunk, W. E. X-34, a fluorescent derivative of Congo red: a novel histochemical stain for Alzheimer's disease pathology. J Histochem Cytochem 48, 1223-1232 (2000).
Klunk, W. E. et al. Imaging Abeta plaques in living transgenic mice with multiphoton microscopy and methoxy-X04, a systemically administered Congo red derivative. J Neuropathol Exp Neurol 61, 797-805 (2002).
Mathis, C. A. et al. A lipophilic thioflavin-T derivative for positron emission tomography (PET) imaging of amyloid in brain. Bioorg Med Chem Lett 12, 295-298 (2002).
Aslund, A. et al. Novel pentameric thiophene derivatives for in vitro and in vivo optical imaging of a plethora of protein aggregates in cerebral amyloidoses. ACS Chem Biol 4, 673-684 (2009).
Nilsson, K. P., Herland, A., Hammarstrom, P. & Inganas, O. Conjugated polyelectrolytes: conformation-sensitive optical probes for detection of amyloid fibril formation. Biochemistry 44, 3718-3724 (2005).
Hammarstrom, P. et al. A fluorescent pentameric thiophene derivative detects in vitro-formed prefibrillar protein aggregates. Biochemistry 49, 6838-6845 (2010).
Oakley, H. et al. Intraneuronal beta-amyloid aggregates, neurodegeneration, and neuron loss in transgenic mice with five familial Alzheimer's disease mutations: potential factors in amyloid plaque formation. J Neurosci 26, 10129-10140 (2006).
Caumartin, J., Lemaoult, J. & Carosella, E. D. Intercellular exchanges of membrane patches (trogocytosis) highlight the next level of immune plasticity. Transpl Immunol 17, 20-22 (2006).
Thambisetty, M. & Lovestone, S. Blood-based biomarkers of Alzheimer's disease: challenging but feasible. Biomark Med 4, 65-79 (2010).
van Rossum, I. A. et al. Injury markers predict time to dementia in subjects with MCI and amyloid pathology. Neurology (2012).
Jack, C. R. J. Alzheimer disease: new concepts on its neurobiology and the clinical role imaging will play. Radiology 263, 344-361 (2012).
Matsuda, H. & Imabayashi, E. Molecular neuroimaging in Alzheimer's disease. Neuroimaging Clin N Am 22, 57-65, viii (2012).
Nordstedt, C. et al. Human neutrophil phagocytic granules contain a truncated soluble form of the Alzheimer beta/A4 amyloid precursor protein (APP). J Biol Chem 269, 9805-9810 (1994).
Crystal, A.S. et al. A comparison of amyloid fibrillogenesis using the novel fluorescent compound K114. J Neurochem. Sep. 2003;86(6):1359-68.
Li. Q. X. et al. (1999) The amyloid precursor protein of Alzheimer disease in human brain and blood. J Leukoc Biol 66, 567-574.
Zaghi, J. et al. (2009) Alzheimer disease macrophages shuttle amyloid-beta from neurons to vessels, contributing to amyloid angiopathy. Acta Neuropathol 117, 111-124.
Pasternak, S. H., Callahan, J. W. and Mahuran, D. J. (2004) The role of the endosomal/lysosomal system in amyloid-beta production and the pathophysiology of Alzheimer's disease: reexamining the spatial paradox from a lysosomal perspective. J Alzheimers Dis 6, 53-65.
Fiala, M. et al. (2007) Phagocytosis of amyloid-beta and inflammation: two faces of innate immunity in Alzheimer's disease. J Alzheimers Dis 11, 457-463.
Rezai-Zadeh, K. et al. (2009) Can peripheral leukocytes be used as Alzheimer's disease biomarkers? Expert Rev Neurother 9, 1623-1633.
Klingstedt, T. et al. (2012) Luminescent conjugated poly- and oligo-thiophenes: optical ligands for spectral assignment of a plethora of protein aggregates, Biochemical Society Transactions, vol. 40, part 4, pp. 704-710.
Nilsson, K. et al., "Conjugated polyelectrolytes: conformation-sensitive optical probes for detection of amyloid fibril formation." Biochemistry, 2005, vol. 44, No. 10, pp. 3718-3724.
Engel, V. et al., "Sporadic inclusion-body myositis and its similarities to Alzheimer disease brain: recent approaches to diagnosis and pathogenesis, and relation to aging." Scandinavian Journal of Rheumatology, 1998, vol. 27, No. 6, pp. 389-405.
Schall, U., "Effekte von Interferonen auf die Phagozytosekapazitat von mononuklearen Phagozyten bei Alzheimer Erkrankung." Diss. Saarbrucken, Univ., Diss., 2010, 2008.
International Search Report and Written Opinion for International PCT Application No. PCT/CA2014/000250 dated Jul. 3, 2014.
Kiko, T. et al., "Amyloid β Levels in Human Red Blood Cells." PLOS One, Nov. 2012, vol. 7, Issue 11, e49620, pp. 1-6.
Lan, J. et al., "The peripheral blood of Aβ binding RBC as a biomarker for diagnosis of Alzheimer's disease." Age and Ageing, 2015, 44, pp. 458-464.
Galasko, D. and Golde, T.E., "Biomarkers for Alzheimer's disease in plasma, serum and blood—conceptual and practical problems." Alzheimer's Research and Therapy, 2013, 5:10.
Askanas, V. and Engel, W.K. et al., "Sporadic inclusion—body myositis and its similarities to Alzheimer disease brain: recent approaches to diagnosis and pathogenesis, and relation to aging." Scandinavian Journal of Rheumatology, 1998, vol. 27, No. 6, pp. 389-405.
Barnes, D.E. and Yaffe, K., "The projected effect of risk factor reduction on Alzheimer's disease prevalence." Lancet Neurol. (2011), 10, 819-828.
Selkoe, D.J., "Alzheimer's disease: genes, proteins, and therapy." Physiol Rev. (2001), vol. 81, No. 2, 741-766.
De La Torre, J.C., "Alzheimer disease as a vascular disorder: nosological evidence." Stroke (2002), 33, 1152-1162.
Deane, R. and Zlokovic, B.V., "Role of the blood-brain barrier in the pathogenesis of Alzheimer's disease." Curr Alzheimer Res. (2007), 4, 191-197.
Mildner, A. et al., "Microglia in the adult brain arise from Ly-6ChiCCR2+ monocytes only under defined host conditions." Nat Neurosci. (2007), 10, 1544-1553.
Stamatovic, S.M. et al., "Monocyte chemoattractant protein-1 regulation of bloodbrain barrier permeability." J Cereb Blood Flow Metab. (2005), 25, 593-606.
Mapstone, M. et al., "Plasma phospholipids identify antecedent memory impairment in older adults." Nature Medicine (published online Mar. 9, 2014) doi:10.1038/nm.3466.
Senanarong, V. et al., "Alzheimer's disease dementia as the diagnosis best supported by the cerebrospinal fluid biomarkers: difference in cut-off levels from thai experience." Int J Alzheimers Dis. (2012), 212063.
Vicart, P. et al., "A missense mutation in the αB-crystallin chaperone gene causes a desmin-related myopathy." Nature Genetics, (1998), 20, 92-95.
Goebel, H.H. and Muller, H.D., "Protein aggregate myopathies." Seminars in Pediatric Neurology (2006), 96-103.
Stys, P.K. et al., "Will the real multiple sclerosis please stand up?" Nat Rev Neurosci., Jul. 2012; 13(7):507-14.
Corder, E.H. et al., "Gene dose of apolipoprotein E type 4 allele and the risk of Alzheimer's disease in late onset families." Science (1993), 261, 921-923.
Blennow, K. et al., "Cerebrospinal fluid and plasma biomarkers in Alzheimer disease." Nat Rev Neurol. (2010), 6, 131-144.

\* cited by examiner

METHODS FOR ANALYZING BLOOD TO DETECT DISEASES ASSOCIATED WITH ABNORMAL PROTEIN AGGREGATION

FIELD

The disclosure relates to methods for analyzing blood to detect diseases associated with abnormal protein aggregation. In one embodiment, the disease associated with abnormal protein aggregation is Alzheimer's disease.

BACKGROUND

Alzheimer's disease (AD) is the most common cause of dementia in elderly populations throughout the world with more than 35 million people affected, and is projected to rise to 115 million by 2050 if effective therapeutics are not developed (Barnes and Yaffe, 2011). This age-related neurodegenerative disorder is pathologically characterized by amyloid β (Aβ)-containing senile plaques, neurofibrillary tangles, and synapse loss in the brain (Selkoe 2001). Although it is clear that AD is a degenerative disorder, the role of the immune system is prominent (reviewed in Britschgi and Wyss-Coray 2007). In AD, toxic Aβ peptides aggregate into higher molecular weight assemblies and accumulate not only in the extracellular space, but also in the walls of blood vessels in the brain (de la Torre 2002; Deane and Zlokovic 2007), increasing their permeability (Nagababu et al 2009), and promoting transfer of T lymphocytes into brain (Farkas et al 2003). Macrophages/microglia ingest Aβ and are key players for Aβ clearance (Majumdar et al 2008; Mildner et al 2007; Simard et al 2006). Neutrophils also infiltrate into AD brain by virtue of blood brain barrier disruption (Stamatovic et al 2005).

Despite considerable effort, there neither a cure for AD, nor even a clinical test to reliably establish the diagnosis with certainty; post-mortem examination of brain tissue is currently the only certain way to confirm the diagnosis of AD. In fact, current diagnostic criteria have "Probable AD" as the category with the highest certainty (McKhann et al 2011), reflecting the limitations in ante-mortem diagnosis. A simple and reliable test would be important for several reasons: therapeutic trials will be more reliable if enrolled subjects have a definitive diagnosis, allowing a more homogeneous population to be studied. Milder cases of dementia (mild cognitive impairment), where diagnostic criteria for AD are not yet met, could be correctly classified as early AD vs. other causes (e.g. vascular), allowing better prognostication and institution of proper treatment, once this becomes available.

From a population health perspective, given that biochemical changes in AD brain (e.g. amyloid deposition) begin years to perhaps decades before clinical symptoms, it may be possible to detect early pre-clinical disease and institute preventive measures when available. Thus, development of an inexpensive, non-invasive, rapid test for AD is of paramount importance as the developed world braces for this inevitable epidemic.

Much effort has gone into developing biomarkers to support an AD diagnosis. In the blood, focus has been on measuring Aβ levels in the plasma. This has not proved reliable, as levels of Aβ40, Aβ42, or ratios of the two, cannot reliably separate healthy controls from AD patients (Thambisety and Lovestone 2010). Other approaches include proteornics analysis of plasma, but this is expensive, complex, not amenable to high throughput assays, and remains experimental. CSF analysis of Aβ and (phosphorylated) tau levels has stronger predictive value (van Rossum et al 2012; Senanaron et al 2012), but compared to blood is invasive and unlikely to become routine outside of formal research trials. Imaging markers (MRI, fMRI, FDG-PET, amyloid-PET) (Jack 2012; Matsuda and lmabayashi 2012) are all more expensive, not universally available, and are either non-specific (MRI) or highly specialized and available in only a few centers (e.g, amyloid-PET). Therefore, a simple and inexpensive blood test to diagnose AD and AD-related mild cognitive impairment that will progress to AD, is highly desirable. An ability to perform detection from small samples of human blood would be a tremendous improvement over current methods, and pave the way for developing a simple, rapid high-throughput screening method. Such methods would also be applicable to other diseases characterized by abnormal protein aggregation.

SUMMARY

The inventors describe a novel method for analyzing leukocytes to detect diseases associated with abnormal protein aggregation.

Accordingly, the disclosure relates to a method of detecting a disease associated with abnormal protein aggregation in a subject, comprising a method of detecting a disease associated with abnormal protein aggregation in a subject, comprising (a) contacting leukocytes from the subject with a probe that binds to pathogenic protein aggregates, and (b) detecting the probe bound to the pathogenic protein aggregates, wherein the presence of pathogenic protein aggregates in the leukocytes is indicative that the subject has a disease associated with abnormal protein aggregation.

In one embodiment, the method comprises:
  a) obtaining a blood sample from the subject;
  b) isolating leukocytes from the blood sample; and
  c) contacting the leukocytes with a probe that binds to pathogenic protein aggregates.

In another embodiment, the method comprises:
  a) obtaining a blood sample comprising buffy coat from the subject; and
  b) contacting the leukocytes of the buffy coat with a probe that binds to pathogenic protein aggregates.

In another embodiment, the probe is a fluorescent probe, optionally a conformationally-sensitive probe. Optionally, the probe is Congo Red, a Congo Red derivative, K114, X34, BSB, FSB, IMSB, Chrysamine-G, methoxy-X34, methoxy-X04, thioflavin-T, thioflavin-S, Pittsburgh compound B, thiazine red R, auramine-O, p-FTAA or a luminescent conjugated polythiophene (LCP) or luminescent conjugated oligothiophene (LCO) related to p-FTAA.

In another embodiment, detecting the probe bound to the pathogenic protein aggregates comprises detecting the fluorescence or absorbance of the probe bound to the pathogenic protein aggregates.

In another embodiment, detecting the fluorescence or absorbance of the probe comprises detecting the intensity of the fluorescence signal, generating a fluorescence emission spectrum and/or generating an absorption spectrum.

In another embodiment, the method further comprises comparing the fluorescence or absorbance of the probe contacted with the leukocytes to the fluorescence or absorbance of the reference probe contacted with reference leukocytes. Optionally, the reference leukocytes are from a reference subject who has a disease associated with abnormal protein aggregation, and correspondence between the fluorescence or absorbance of the subject leukocytes and the fluorescence or absorbance of the reference leukocytes indicates that the subject has a disease associated with abnormal protein aggregation.

In another embodiment, the method further comprises comparing the fluorescence emission spectrum to one or more reference fluorescence emission spectra. Optionally, at least one reference emission spectrum is a fluorescent emission spectrum from reference leukocytes from a reference subject who has a disease associated with abnormal protein aggregation, and correspondence between the fluorescence emission spectrum and the at least one reference fluorescence emission spectrum indicates that the subject has a disease associated with abnormal protein aggregation.

In another embodiment, the method further comprises comparing the absorption spectrum to one or more reference absorption spectra. Optionally, at least one reference absorption spectrum is an absorption spectrum from reference leukocytes from a reference subject who has a disease associated with abnormal protein aggregation, and correspondence between the absorption spectrum and the at least one reference absorption spectrum indicates that the subject has a disease associated with abnormal protein aggregation.

In another embodiment, the method further comprises:
(a) generating a fluorescence emission spectrum or absorption spectrum;
(b) performing spectral unmixing to determine the weightings of individual basis spectra that contribute to the fluorescence emission spectrum or absorption spectrum; and
(c) using the weightings to determine a probability that the subject has a disease associated with abnormal protein aggregation.

In another embodiment, the individual basis spectra are determined from (a) samples of subjects known to have a disease associated with abnormal protein aggregation, (b) samples of healthy control subjects and/or (c) samples that have not been contacted with the probe.

In another embodiment, the spectral unmixing is performed using the Levenberg-Marquardt algorithm.

In another embodiment, the probe is an antibody to the pathogenic protein aggregates, optionally an anti β-amyloid antibody.

In another embodiment, the disease associated with abnormal protein aggregation is selected from the group consisting of: Alzheimer's disease, Parkinson's disease, Huntington's disease, mild cognitive impairment, cerebral amyloid angiopathy, myopathy, neuropathy, brain trauma, frontotemporal dementia, Pick's disease, multiple sclerosis, prion disorders and Down's syndrome.

In another embodiment, the pathogenic protein aggregates comprise amyloid proteins, optionally β-amyloid, α-synuclein, huntingtin, tau protein, hyperphosphorylated tau protein (pTau), prion protein, αB-crystallin (CRYAB), desmin, selenoproteins, actin and/or myosin. In another embodiment, the pathogenic protein aggregates comprise β-amyloids and the disease is Alzheimer's disease.

The disclosure also relates to a method for evaluating leukocytes derived from a subject who may have or has a disease associated with abnormal protein aggregation comprising:
a) obtaining a test blood sample from the subject,
b) isolating leukocytes from the test blood sample,
c) contacting the leukocytes with a probe that binds to pathogenic protein aggregates in the leukocytes, and
d) detecting the probe bound to the pathogenic protein aggregates,
wherein the presence of pathogenic protein aggregates in the leukocytes is indicative that the subject has a disease associated with abnormal protein aggregation.

In one embodiment, the probe is a fluorescent probe, optionally a conformationally-sensitive probe.

In another embodiment, the probe is Congo Red, a Congo Red derivative, K114, X34, BSB, FSB, IMSB, Chrysamine-G, methoxy-X34, methoxy-X04, thioflavin-T, thioflavin-S, Pittsburgh compound B, thiazine red R, auramine-O or p-FTAA, a luminescent conjugated polythiophene (LCP) or luminescent conjugated oligothiophene (LCO) related to p-FTAA.

In another embodiment, detecting the probe bound to the pathogenic protein aggregates comprises detecting the fluorescence or absorbance of the probe bound to the pathogenic protein aggregates.

In another embodiment, detecting the fluorescence or absorbance comprises detecting the intensity of the fluorescence signal, generating a fluorescence emission spectrum or generating an absorption spectrum.

In another embodiment, the disease associated with abnormal protein aggregation is selected from the group consisting of: Alzheimer's disease, Parkinson's disease, Huntington's disease, mild cognitive impairment, cerebral amyloid angiopathy, myopathy, neuropathy, brain trauma, frontotemporal dementia, Pick's disease, multiple sclerosis, prion disorders and Down's syndrome.

In another embodiment, the pathogenic protein aggregates comprise amyloid proteins, optionally β-amyloid, α-synuclein, huntingtin, tau protein, hyperphosphorylated tau protein (pTau), prion protein, αB-crystallin (CRYAB), desmin, selenoproteins, actin and/or myosin.

In another embodiment, the pathogenic protein aggregates comprise β-amyloids and the disease is Alzheimer's disease.

The disclosure also relates to a kit for analyzing leukocytes to detect a disease associated with abnormal protein aggregation comprising:
(a) a probe that detects the presence of pathogenic protein aggregates in the leukocytes and
(b) instructions for use.

In one embodiment, the probe is a fluorescent probe, optionally Congo Red, a Congo Red derivative, K114, X34, BSB, FSB, IMSB, Chrysamine-G, methoxy-X34, methoxy-X04, thioflavin-T, thioflavin-S, Pittsburgh compound B, thiazine red R, auramine-O or p-FTAA or a luminescent conjugated polythiophene (LCP) or luminescent conjugated oligothiophene (LCO) related to p-FTAA.

In another embodiment, the disease associated with abnormal protein aggregation is selected from the group consisting of: Alzheimer's disease, Parkinson's disease, Huntington's disease, mild cognitive impairment, cerebral amyloid angiopathy, myopathy, neuropathy, brain trauma, frontotemporal dementia, Pick's disease, multiple sclerosis, prion disorders and Down's syndrome.

In another embodiment, the pathogenic protein aggregates comprise amyloid proteins, optionally β-amyloid, α-synuclein, huntingtin, tau protein, hyperphosphorylated tau protein (pTau), prion protein, αB-crystallin (CRYAB), desmin, selenoproteins, actin and/or myosin.

Other features and advantages of the disclosure will become apparent from the following detailed description. It should be understood, however, that the description and the specific examples while indicating preferred embodiments are given by way of illustration only, since various changes and modifications within the spirit and scope of the disclosure will become apparent to those skilled in the art from this description of various embodiments.

DRAWINGS

Embodiments are described below in relation to the drawings in which:

FIG. 1 depicts spectral fluorescence images of X-34, a fluorescent amyloid probe (Styren et al. 2000), upon binding to senile plaques in formalin-fixed sections from 5×FAD, AD transgenic mouse brains. 32 channels of spectrally resolved data are collected for each pixel. a) Unmixed image showing typical morphology of amyloid plaques and two states of plaque "maturity". b) Measured emission spectra from plaque and laser backscatter used in the mathematical unmixing operation. The closely spaced emissions of the core and edge of a large amyloid plaque in the X-34 image were well separated as shown in c and d. These results illustrate the ability not only to detect amyloid plaques in brain, but to be able to distinguish various aggregation states within a single plaque.

Figure 2:
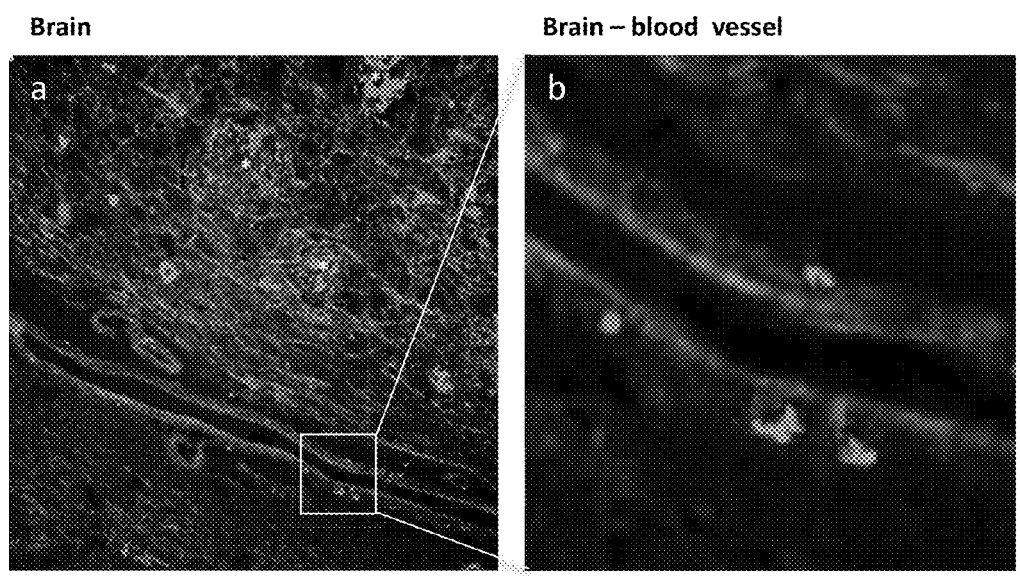

FIG. 2 shows anti-Aβ (6E10) immunofluorescence in formalin-fixed sections from 5×FAD mouse brain. a) Typical morphology of senile plaques which is 6E10 immunopositive (asterisks). 6E10-positive blood cells are also observed around a blood vessel (Square box). b) High magnification images of the square box from a, showing that the leukocytes contain material that is Aβ.

Figure 3:
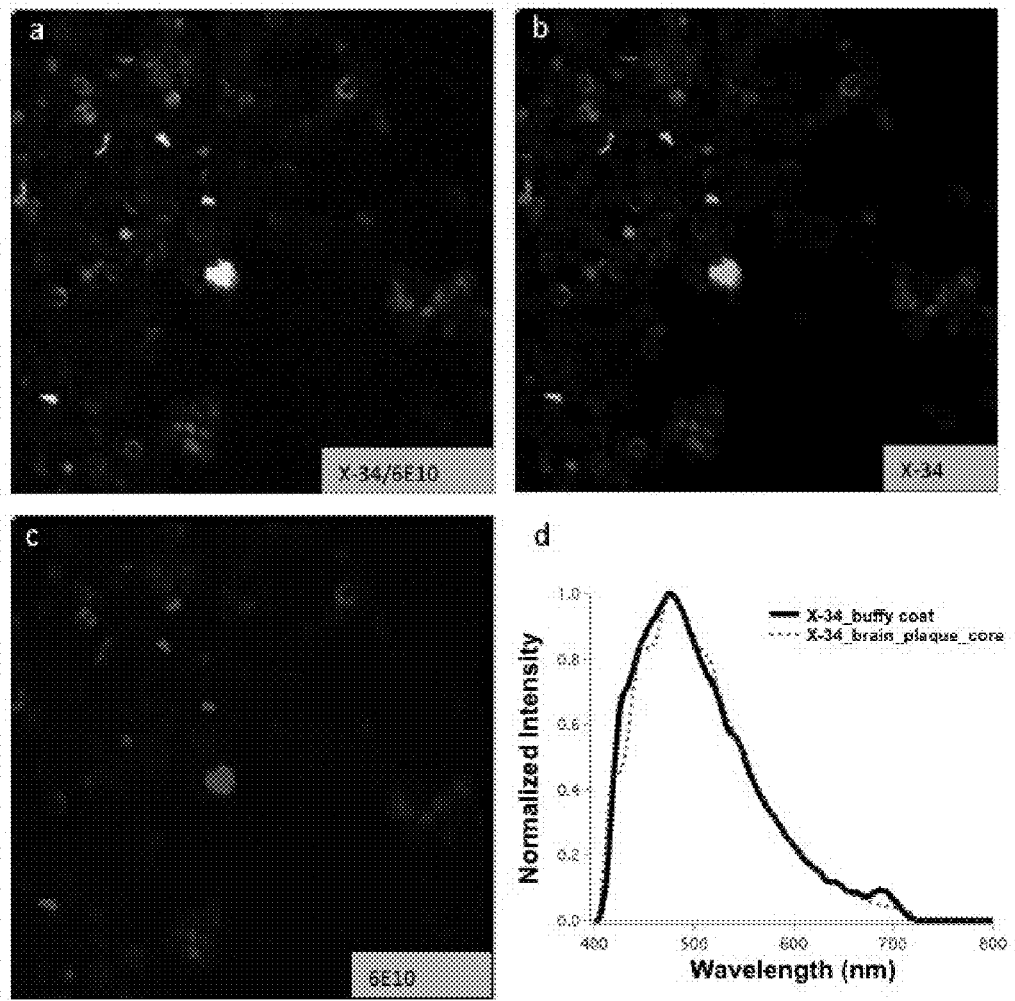

FIG. 3 shows double labeling of X-34 with 6E10 immunofluorescence in mouse buffy coat samples. a-c) Unmixed X-34 image with 6E10 immunofluorescence in 5×FAD mouse buffy coat from circulating blood. X-34-positive cells are clearly co-localized with 6E10 immunofluorescent signals. d) Emission spectra of X-34-positive 5×FAD mouse buffy coat leukocytes. Measured emission spectra of X-34-positive leukocytes from circulating blood are virtually identical to those from senile plaque in 5×FAD mouse brain (dotted line), demonstrating that the leukocytes contain material that is very similar to that found in plaques.

Figure 4:
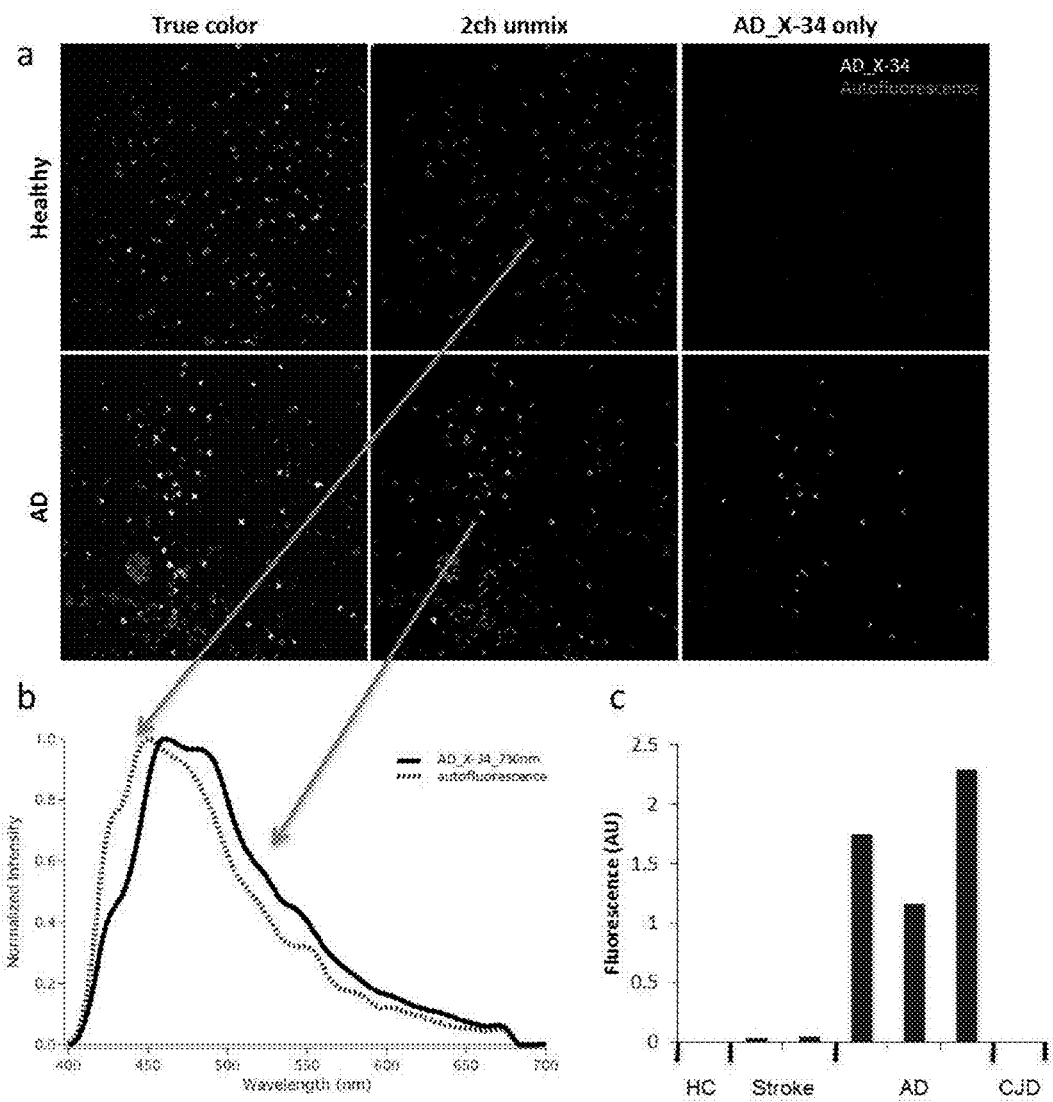

FIG. 4 shows 2-photon spectral fluorescence images of X-34 upon binding to amyloid-like material in buffy coat from healthy control (HC) and AD patients. a) Truecolor (left column), unmixed autofluorescence (grey) and AD-specific X-34 (white) channels (middle & right columns). AD-specific X-34 signal was detected only from AD buffy coat. b) Emission spectra of AD-specific X-34 signals and autofluorescence. c) A bar graph showing strong AD-specific signal only in AD leukocytes. CJD refers to a patient with Creutzfeldt-Jakob disease.

Figure 5:
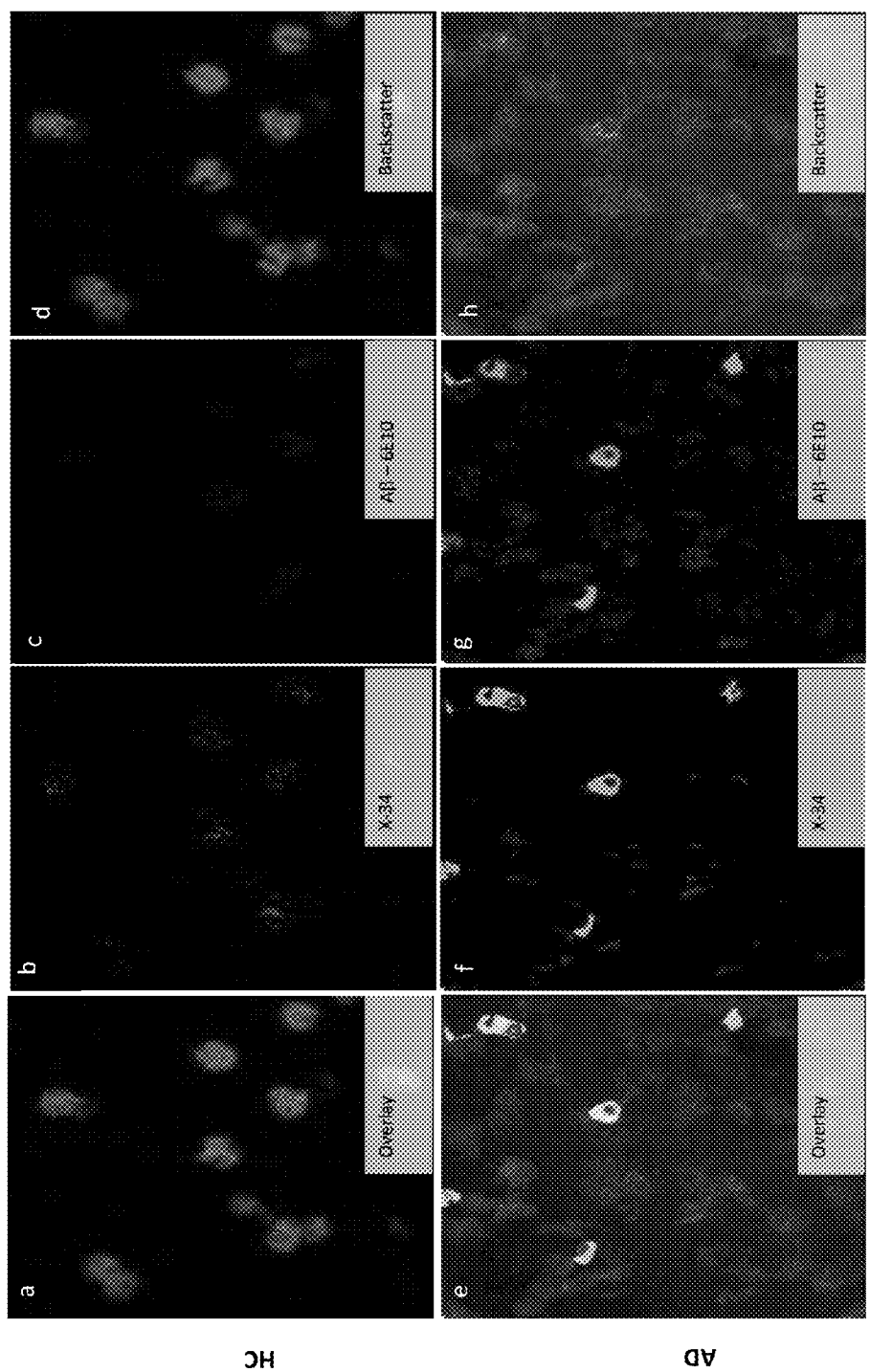

FIG. 5 shows double-labeling using the amyloid probes X-34, with anti-Aβ antibody (6E10) in buffy coat from healthy control (HC) and AD patients. AD-specific X-34 signal (see FIG. 4 for details) is strong only in AD leukocytes (f), which co-localizes with strong Aβ immunolabeling (g). Only a fraction of AD leukocytes were positive however. In contrast, only very weak background signal is seen in the healthy control buffy coat (b, c). Laser backscatter conveniently identifies each cell (d, h), and this signal is perfectly separated from the other emissions using the spectral techniques described herein.

Figure 6:
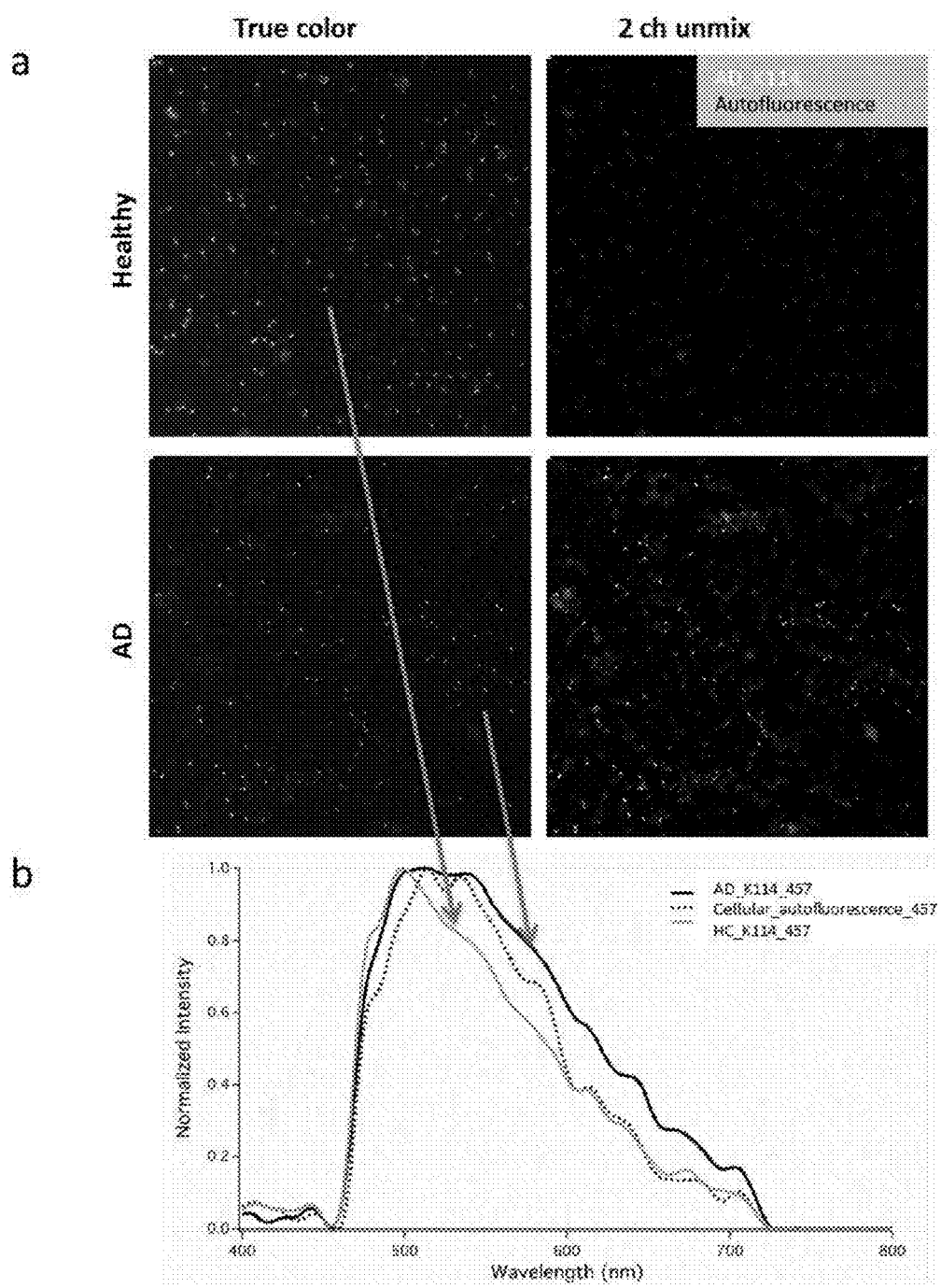

FIG. 6 shows spectral fluorescence images of K114, another fluorescent amyloid probe (Crystal 2003), upon binding to amyloid-like material in buffy coat from healthy control (HC) and AD patients. a) Truecolor (left column), unmixed autofluorescence and AD-specific K114 channels (right column). b) Emission spectra of HC-, AD-specific K114 signals and autofluorescence.

Figure 7:
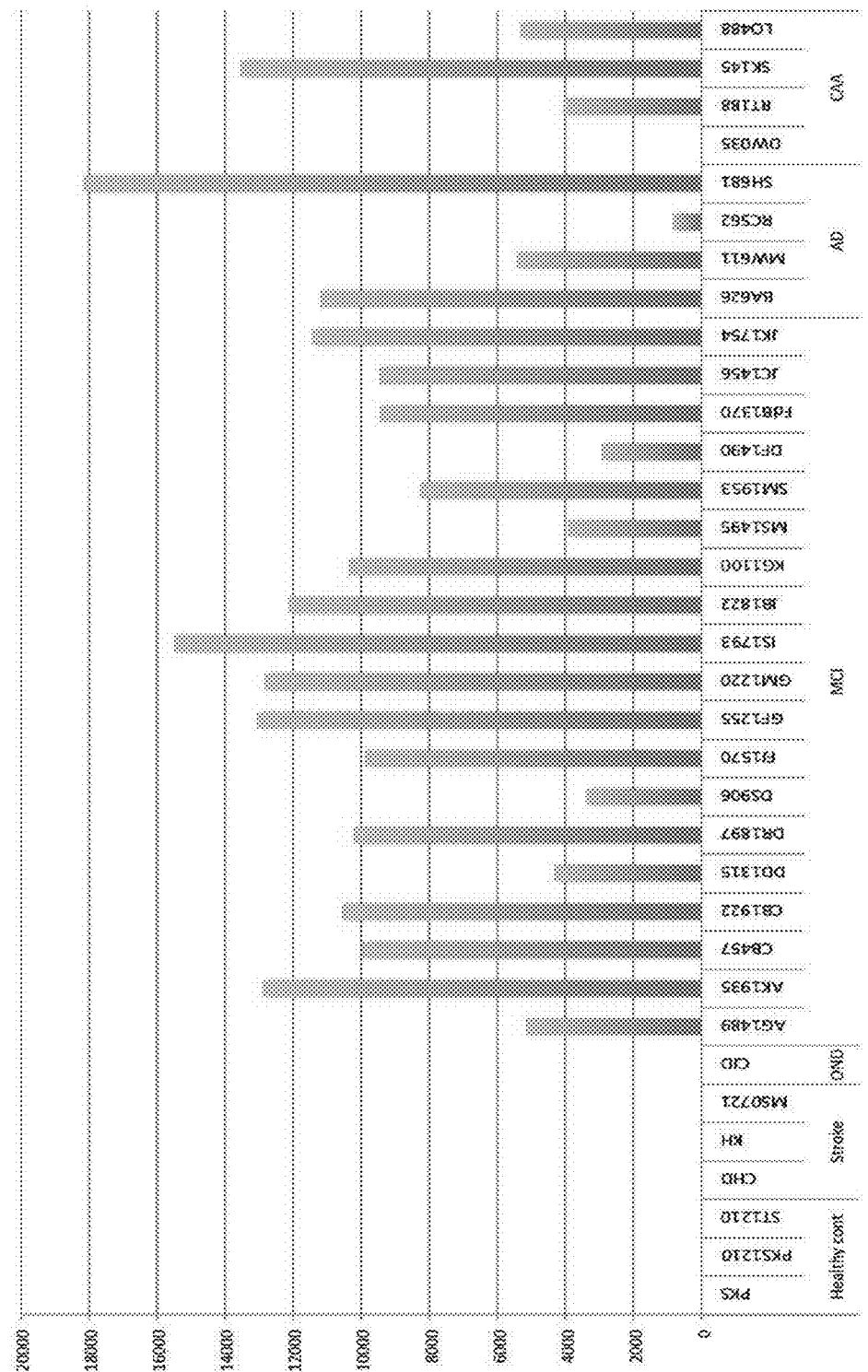

FIG. 7 is a simplified composite index that reflects the probability that a subject (identified on the x-axis) has either AD or Mild Cognitive Impairment (MCI) ("ADR index" ie "AD related index") shown on the y-axis and based on the analysis of spectra using the Levenberg-Marquardt damped least-squares non-linear curve fitting algorithm. Leukocyte cells obtained from patients were labeled with the amyloid probe K114 and spectrally analyzed as described in Example 2.

Figure 8:
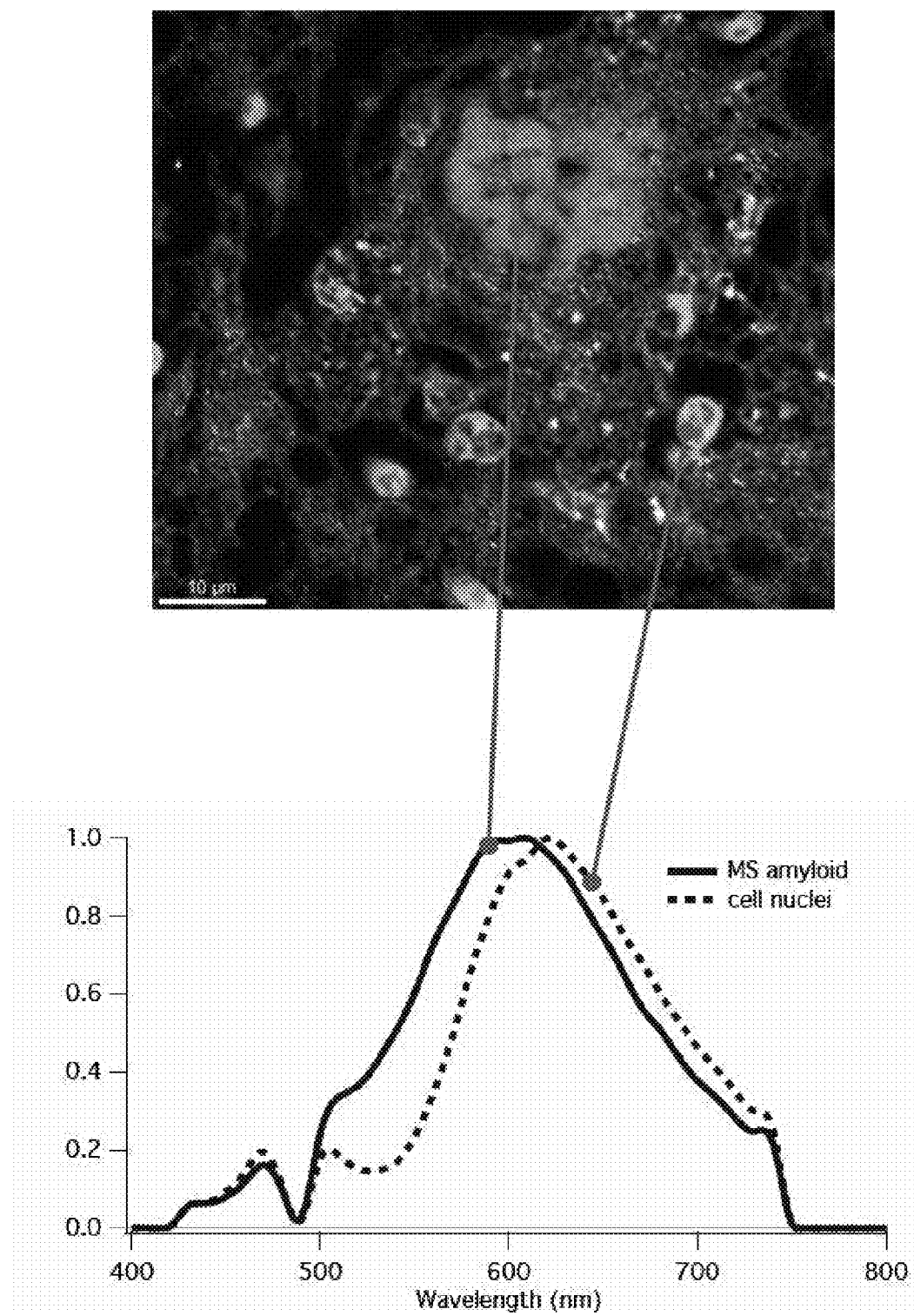

FIG. 8 shows human brain from a multiple sclerosis patient stained with Congo Red. These data suggest that chronic MS plaques have deposits of amyloid, which should be detectable in blood leukocytes, in an analogous manner to AD.

DETAILED DESCRIPTION

The inventors have discovered that the spectral signatures of leukocyte amyloid probe fluorescence from AD subjects are highly similar to those from human and mouse brain senile plaques, thereby demonstrating that leukocytes contain material that is similar to the material found in cerebral plaques. Without being bound by theory, it is postulated that leukocytes exposed to pathogenic protein aggregates accumulate these aggregates. The present methods link the presence of pathogenic protein aggregates in circulating leukocytes to the diagnosis of diseases associated with abnormal protein aggregation.

Accordingly, an aspect of the disclosure provides a method of detecting a disease associated with abnormal protein aggregation in a subject, wherein the presence of pathogenic protein aggregates in the leukocytes of the subject is indicative that the subject has a disease associated with abnormal protein aggregation.

As used herein, the term "disease associated with abnormal protein aggregation" refers to any disease that is associated with and/or characterized by protein misfolding and aggregation. In such diseases, proteins may be misfolded and aggregated from their soluble functional state into highly ordered fibrillar assemblies with high β-sheet content ("amyloid peptides" or "amyloids"). While "diseases associated with abnormal protein aggregation" may be otherwise unrelated, they have in common binding to amyloid probes such as Congo Red. Diseases associated with abnormal protein aggregation include, but are not limited to, Alzheimer's disease, Parkinson's disease, Huntington's disease, mild cognitive impairment, cerebral amyloid angiopathy, brain trauma, frontotemporal dementia, Pick's disease, multiple sclerosis, prion disorders and Down's syndrome. Other disease associated with abnormal protein aggregation include neuromuscular disorders such as myopathies (e.g. desminopathies, alpha-B crystallinopathies, selenoprotein-opathies, hereditary inclusion body myopathies, actinopathies, myosinopathies) (Vicart et al 1998) and neuropathies such as familial amyloidosis neuropathy (Sharma and Goebel 2005). Diseases associated with abnormal protein aggregation also include neurological disorders and/or neurodegenerative disorders, Diseases associated with abnormal protein aggregation are not limited to the specific diseases recited herein; any disease that includes misfolded protein aggregates as part of its pathology may be detected using the methods described herein.

Different proteins may be misfolded and aggregated in different diseases. For example, Alzheimer's disease is characterized by β-amyloid containing plaques that accumulate in brain tissue. In Parkinson's disease, α-synuclein (α-Syn) neuronal inclusions are seen. Huntington's disease is associated with aggregations of the huntingtin protein. The infectious agent responsible for prion disorders such as transmissible spongiform encephalopathy, bovine spongiform encephalopathy and Creutzfeldt-Jakob disease (CJD) is a misfolded and aggregated version of prion protein. Further, the present inventors have evidence that amyloid deposits are found in the brains of multiple sclerosis patients.

As used herein, the term "pathogenic protein aggregates" refers to toxic misfolded and aggregated versions of proteins and polypeptides present in the body. As used herein, the term "protein aggregates" refers to misfolded peptide or protein oligomers, including peptide dimers and oligomers larger than dimers. Examples of "pathogenic protein aggregates" include amyloids. "Amyloids" is a general term used to describe insoluble fibrous protein aggregates. Pathogenic protein aggregates can also comprise soluble aggregates such as β-amyloid oligomers. Pathogenic protein aggregates can be made up of a single protein or multiple different proteins. Pathogenic protein aggregates can also include lipid and nucleic acid components. Examples of proteins that can be found in pathogenic protein aggregates include, but are not limited to, β-amyloid, α-synuclein, huntingtin, tau protein, hyperphosphorylated tau protein (pTau), prion protein, αB-crystallin (CRYAB), desmin, selenoproteins, actin and myosin.

As used herein the phrase "method of detecting a disease associated with abnormal protein aggregation in a subject" refers to a method or process of determining if a subject has a disease associated with abnormal protein aggregation. The phrase "method of detecting a disease associated with abnormal protein aggregation in a subject" also refers to a method of determining if a subject has an increased risk of developing a disease associated with abnormal protein aggregation. The terms "risk" and "increased risk" as used herein refer to a subject having a predisposition to developing a disease e.g increased risk compared to the average risk of a population. The phrase "detecting a disease" also refers to detecting a disease in a pre-symptomatic patient. "Detecting a disease" also includes detecting the stage, severity, subtype or the progression of a disease.

In one embodiment, the methods described herein include obtaining a blood sample from a subject. Methods of obtaining blood samples are well known in the art. In one embodiment, the sample comprises blood, whole blood or a fraction thereof. In another embodiment, the blood sample comprises buffy coat. In a further embodiment, the blood sample comprises leukocytes.

Buffy coat is a fraction of an anticoagulated blood sample following density gradient centrifugation of the blood. The buffy coat contains most of the leukocytes and platelets of the blood. The buffy coat may be isolated from a blood sample using any technique known in the art. Optionally, blood samples may be centrifuged and the buffy coat (or leukocyte band) may be removed. Any contaminating red blood cells are optionally lysed.

As used here, the term "leukocyte" or "white blood cell" refers to a cell of the immune system. Examples of leukocytes include granulocytes such as neutrophils, eosinophils and basophils, lymphocytes, monocytes and macrophages (derivatives of monocytes). In one embodiment, pathogenic protein aggregates are identified in phagocytic blood leukocytes including, but not limited to, monocytes and/or macrophages. Without being bound by theory, it is believed that all major types of leukocytes can potentially accumulate pathogenic Aβ or other misfolded proteins/peptides, then carry these to circulating blood. Phagocytosis by macrophages and neutrophils is a key line of defense, clearing pathogens and waste products. Further, while lymphocytes are not phagocytic, intercellular protein transfer has been observed between these immune cells (termed trogocytosis) (reviewed in Caumartin et al 2006).

As used herein, the term "isolating leukocytes" refers to obtaining a sample comprising leukocytes, consisting of leukocytes or consisting essentially of leukocytes. In one embodiment, isolating leukocytes refers to obtaining a sample that is free of, or substantially free of, non-leukocyte cells. The term "isolating leukocytes" optionally refers to isolating the buffy coat layer of a blood sample. The methods described herein are performed on a sample of leukocytes, such as sample comprising leukocytes, consisting of leukocytes or consisting essentially of leukocytes. In another embodiment, the methods described herein are performed on a buffy coat sample.

In another embodiment, a particular type of leukocyte cell is isolated and the methods described herein are performed on that particular sub-type. Examples of leukocyte cell types include neutrophils, eosinophils and basophils, lymphocytes, NK cells, monocytes and macrophages.

The methods described herein include the identification of pathogenic protein aggregates in the leukocytes of a subject. The presence of pathogenic protein aggregates in leukocytes can be detected using a number of methods. In one embodiment, pathogenic protein aggregates are detected in leukocytes using probes that specifically bind to and/or interact with the pathogenic protein aggregates.

The methods described herein also include the identification of pathogenic protein aggregates associated with the leukocytes of a subject. The presence of pathogenic protein aggregates associated with leukocytes can be detected using a number of methods. As used herein, the term "associated with" leukocytes is used to refer to pathogenic protein aggregates adsorbed or absorbed to the leukocyte cell surface, absorbed into the leukocyte interior, or in separated granules outside of the leukocyte cells.

In one embodiment, pathogenic protein aggregates are detected in leukocytes using probes that specifically bind to and/or interact with the pathogenic protein aggregates. As used herein, the term "probe that binds to pathogenic protein aggregates" includes both direct and indirect binding to the aggregates.

As used herein, the term "probe" refers to any detectable agent that binds, directly or indirectly, to a pathogenic protein aggregate. In one embodiment, the probe is a fluorescent probe or a luminescent probe. A "fluorescent probe" is a probe with the ability to emit light of a certain wavelength when activated by light of another wavelength.

In another embodiment, the probe is a conformationally-sensitive fluorescent or luminescent probe. "Conformationally-sensitive" indicates that the absorption and/or emission spectra of the fluorescent and/or luminescent probe change as a function of the conformation of the target peptide, protein, lipid, nucleic acid, or macromolecular assembly thereof, thereby reporting the conformational states of such assemblies or aggregates. Probes can be engineered to exhibit maximal spectral changes as a function of the conformational state of said macromolecular aggregates to maximize sensitivity and specificity of detection of the pathogenic aggregates.

In another embodiment, the probe specifically binds to amyloid fibrils. Specific examples of conformationally-sensitive fluorescent probes useful for detecting amyloid peptides include, but are not limited to, Congo Red, Congo Red derivatives and bis-styrylbenzenes (e.g. K114, X34, BSB, FSB, IMSB, Chrysamine-G, methoxy-X34, methoxy-X04), thioflavin analogs (thioflavin-T, thioflavin-S, Pittsburgh compound B), thiazine red R, auramine-O, pentameric formyl thiophene acetic acid (p-FTAA) and related luminescent conjugated polythiophenes (LCPs) or luminescent conjugated oligothiophenes (LCOs). As used herein, the term "contacting a cell with a probe" or "labeling a cell with a probe" refers to any means by which a cell is exposed to a probe such that the probe is able to bind pathogenic protein aggregates in the cell (i.e., intracellular protein aggregates) or protein aggregates associated with the cell. In one embodiment, cells are permeabilized prior to contacting with a probe or labeling with a probe. Methods of labeling cells with fluorescent probes are well known in the art. For example, leukocytes are optionally fixed and dried and then stained with a fluorescent probe. The pH, time, concentration and vehicle for the probe may be specific for the probe.

Once the leukocytes are labeled, various methods may be used to detect binding of the fluorescent probe to the protein aggregates. In one embodiment, detecting the probe bound to the pathogenic protein aggregates comprises detecting the fluorescence of the probe bound to the pathogenic protein aggregates. Detecting the fluorescence of the probe may be accomplished by any method known in the art.

In another embodiment, detecting the probe bound to the pathogenic protein aggregates comprises detecting the absorbance of the probe bound to the pathogenic protein aggregates. The "absorbance" of the probe is the amount of light the probe absorbs at any particular wavelength. Detecting the absorbance of the probe may be accomplished by any method known in the art. In another embodiment, detecting the absorbance of the probe comprises generating an absorption spectra.

In one embodiment, probe fluorescence or absorbance is spectrally resolved using a spectrometer. The spectrometer is optionally an imaging or a non-imaging spectrometer. In another embodiment, a wide-field spectral camera is used to detect probe emission.

In one embodiment, fluorescence or absorbance is detected using fluorescence spectroscopy. In one embodiment, spectral 2-photon imaging is used. For example, spectral 2-photon imaging may be performed with a conventional narrow-band ultrafast laser (e.g. Chameleon, Coherent Inc.) or ultrabroadband femtosecond laser (Octavius, Thorlabs) and a spectral laser-scanning microscope such as the Nikon A1RMP. In another embodiment, spectral 1-photon imaging is used. One or several excitation wavelengths may be used to excite the fluorescent probes. Images are analysed using various programs such as the program ImageTrak (http://www.ucalgary.ca/styslab/imagetrak).

In another embodiment, fluorescence or absorbance is detected using a non-imaging spectrometer such as from a cuvette, small sample holder or a multi-well plate. Here, the labeled cells are suspended, excited by one or more laser lines, and the emission is collected with a (non-imaging) spectrometer.

In yet another embodiment, fluorescence or absorbance is detected using single-cell spectral analysis as in a FACS analyzer. In another embodiment, a microplate reader is used.

In one embodiment, detecting the fluorescence of the probe comprises detecting the intensity of the fluorescence signal from the probe. In another embodiment, detecting the fluorescence of the probe comprises detecting the intensity of the protein-aggregate specific fluorescence from the probe. The term "protein aggregate specific fluorescence" refers to fluorescence from a probe that binds to protein aggregates that is specific for the pathogenic protein aggregates and is not attributable to background fluorescence, autofluorescence or normal state protein.

In another embodiment, detecting the absorbance of the probe comprises detecting the degree, intensity, or quantity of the absorption by the probe. In another embodiment, detecting the absorption of the probe comprises detecting the intensity, degree or quantity of the protein-aggregate specific absorbance by the probe. The term "protein aggregate specific absorbance" refers to absorbance by a probe that binds to protein aggregates that is specific for the pathogenic protein aggregates and is not attributable to background absorption, autoabsorption or normal state protein.

The methods optionally further comprise comparing the fluorescence or absorbance of the probe to the fluorescence or absorbance of a reference probe contacted with reference leukocytes. Preferably, the reference probe and the probe used to contact the subject leukocytes is the same probe.

In one embodiment, reference leukocytes, or control leukocytes, are leukocytes derived from a reference subject who has a disease associated with abnormal protein aggregation. In another embodiment, reference leukocytes, or control leukocytes, are leukocytes derived from a reference subject who does not have a disease associated with abnormal protein aggregation. The reference leukocytes are optionally tested at the same time as the subject leukocytes. In another embodiment, the reference leukocytes are tested at different time from the subject leukocytes. As used herein, the term "subject leukocytes" refers to leukocytes derived from a test subject.

Correspondence, or similarity, between the fluorescence or absorbance of subject leukocytes and the fluorescence or absorbance of reference leukocytes from a reference subject who has a disease associated with abnormal protein aggregation indicates that the subject has a disease associated with abnormal protein aggregation. Differences between the fluorescence or absorbance of subject leukocytes and the fluorescence or absorbance of the reference leukocytes from a reference subject who has a disease associated with abnormal protein aggregation indicates that the subject does not have a disease associated with abnormal protein aggregation.

Likewise, correspondence, or similarity, between the fluorescence or absorbance of subject leukocytes and the fluorescence or absorbance of the reference leukocytes from a reference subject who does not have a disease associated with abnormal protein aggregation indicates that the subject does not have a disease associated with abnormal protein aggregation.

Correspondence, or similarity, between the fluorescence or absorbance of subject leukocytes and the fluorescence or absorbance of reference leukocytes is optionally determined by the amount of fluorescence, the intensity of the fluorescence or the nature of the fluorescence or the degree of absorbance. In another embodiment, correspondence, or similarity, between the fluorescence or absorbance of subject leukocytes and the fluorescence or absorbance of reference leukocytes is determined by analyzing fluorescence emission spectra or absorption spectra, for example by identifying similar fluorescence emission spectrum or absorption spectrum patterns or similar peaks and troughs in the fluorescence emission spectra or absorption spectra.

In another embodiment, the identification of an increase in fluorescence or absorbance, optionally a statistically significant increase in fluorescence or absorbance, of subject leukocytes compared to reference leukocytes from a patient who does not have a disease associated with abnormal protein aggregation indicates that the test subject has a disease associated with abnormal protein aggregation.

In another embodiment, the identification of a similar amount of fluorescence or absorbance from subject leukocytes compared to reference leukocytes from a patient who has a disease associated with abnormal protein aggregation indicates that the test subject has a disease associated with abnormal protein aggregation. In one embodiment, a "similar amount" of fluorescence or absorbance refers to no statistically significant difference in fluorescence or absorbance.

In one embodiment, an increase or decrease in fluorescence can be determined visually by looking at spectral fluorescence images. Increased fluorescence or absorbance can also be quantified. In one embodiment, at least a 10%, 25%, 50%, 75% or 100% increase in fluorescence or absorbance from subject leukocytes compared to reference leukocytes from a patient who does not have a disease associated with abnormal protein aggregation indicates that the test subject has a disease associated with abnormal protein aggregation. In another embodiment, at least a 10%, 25%, 50%, 75% or 100% decrease in fluorescence or absorbance from subject leukocytes compared to reference leukocytes from a patient who has a disease associated with abnormal protein aggregation indicates that the test subject does not have a disease associated with abnormal protein aggregation.

The use of fluorescence or absorbance spectroscopy also allows spectral signatures or fluorescence emission spectra or absorption spectra to be generated from leukocytes labeled with a fluorescent probe. A fluorescence emission spectrum or absorption spectrum plots the normalized intensity of the fluorescent or absorbance signal from the probe against the wavelength for a given sample. The fluorescence emission spectrum or absorption spectrum thereby provides a specific fluorescent or absorbance signature for a given sample.

In one embodiment, the present methods include comparing the fluorescence emission spectrum or absorption spectrum of subject leukocytes to the fluorescence emission spectrum or absorption spectrum of one or more reference leukocytes.

Correspondence, or similarity, between the fluorescence emission spectrum or absorption spectrum of subject leukocytes and a reference fluorescence emission spectrum or absorption spectrum of leukocytes from a reference subject who has a disease associated with abnormal protein aggregation indicates that the subject has a disease associated with abnormal protein aggregation. Correspondence, or similarity, between the fluorescence emission spectrum or absorption spectrum of subject leukocytes and a reference fluorescence emission spectrum or absorption spectrum of leukocytes from a reference subject who does not have a disease associated with abnormal protein aggregation indicates that the subject does not have a disease associated with abnormal protein aggregation. As used herein, correspondence, or similarity, between fluorescence emission spectra or absorption spectra is determined, for example by identifying similar fluorescence emission spectrum or absorption spectrum patterns or similar peaks or troughs in the fluorescence emission spectra or absorption spectrum. In one embodiment, fluorescence emission spectra or absorption spectrum correspond if at least 60, 70, 80, 90 or 95% of the spectral signatures overlap or substantially overlap.

It has been shown that the spectral signatures of the leukocyte amyloid probe fluorescence from AD subjects are similar to those from human and mouse brain senile plaques. Thus, in another embodiment, a reference fluorescence emission spectrum or absorption spectrum is the fluorescence emission spectrum or absorption spectrum from a labeled plaque sample derived from a subject who has a disease associated with abnormal protein aggregation. Optionally, the plaque sample is from an AD-related plaque from a subject with AD. If the fluorescence emission spectrum or absorption spectrum of the test sample corresponds to, or is similar to, the reference emission spectrum or absorption spectrum from the plaque sample, then the test sample comprises pathogenic protein aggregates and/or the test subject has a disease associated with abnormal protein aggregation.

In another embodiment, fluorescence emission spectra or absorption spectra are analyzed to generate an index indicating disease probability. Here, the spectra are analyzed as described below to extract the various components and an index indicating disease probability is assigned. A score consisting of specific emission spectra or absorption spectra, above a particular threshold, indicates that the test cell sample comprises pathogenic protein aggregates and/or the test subject has a disease associated with abnormal protein aggregation.

In one embodiment, a numerical score based on fluorescence emissions or absorbance is calculated. The numerical score reflects the probability that a test cell sample originated from a patient with a disease associated with abnormal protein aggregation. Here, spectral 1-photon confocal or 2-photon images are acquired and fluorescence and/or absorbance signals from leukocytes are processed using algorithms (for example, algorithms based on the Levenberg-Marquardt damped least-squares non-linear curve fitting algorithm, or linear algebraic unmixing/decomposition algorithms) to separate disease-specific signals from background and auto-fluorescence emission. Quantitative fluorescence/absorbance data is extracted thereby allowing the reliable identification of disease versus non-disease samples. In one embodiment, the mathematical method generates numerical scores associated with samples that originate from a subject who has a disease associated with abnormal protein aggregation and numerical scores associated with samples that originate from a subject who does not have a disease associated with abnormal protein aggregation. In one embodiment, the difference between the disease-associated and non-disease associated numerical scores is large enough to allow the classification of test samples as disease-associated or non-disease associated.

In one embodiment, the fluorescence emission spectrum or absorption spectrum acquired from leukocytes contacted with the fluorescent probes described herein is a linear composite of individual basis spectra generated by different species of misfolded proteins, cellular autofluorescence and background signal. These basis spectra contribute different intensities to the overall composite, which is a linear sum of the contributing spectra. The unmixing operation is designed to calculate in a quantitative manner, the relative contributions of each basis spectrum to the overall composite. Once basis spectra are determined from standard samples (for example, known healthy controls, known patients with a disease associated with abnormal protein aggregation such as AD, cellular autofluorescence from unstained samples), the composite spectrum is unmixed using the Levenberg-Marquardt algorithm to determine the weightings of each basis spectrum that contributed to the composite. These weighting coefficients are then used to calculate the various indexes that indicate the probability that any one sample originated from a healthy or diseased subject.

Accordingly, in one embodiment, the methods comprise:
a. generating a fluorescence emission spectrum or absorption spectrum from subject leukocytes;
b. performing spectral unmixing to determine the weightings of individual basis spectra that contribute to the fluorescence emission spectrum or absorption spectrum; and
c. using the weightings to determine a probability that the subject has a disease associated with abnormal protein aggregation.

As used herein, the term "spectral unmixing" refers to any method by which individual basis spectra are separated from the composite fluorescence emission spectrum or absorption spectrum. In one embodiment, spectral unmixing is performed using the Levenberg-Marquardt algorithm. In another embodiment, spectral unmixing is performed using a linear decomposition algorithm.

In one embodiment, the individual basis spectra are determined from samples of (a) subjects known to have a disease associated with abnormal protein aggregation, (b) healthy control subjects and (c) samples that have not been contacted with the probe. Optionally, the individual basis spectra are determined from leukocyte samples.

A person of skill in the art would readily be able to use the method described above to assess the probability that the subject has a disease associated with abnormal protein aggregation.

In another embodiment, spectral analysis of leukocyte samples may be performed at different time points to detect differences in the maturity of the deposits thereby predicting the stage, severity or rate of progression of the underlying disease.

The presence of pathogenic protein aggregates in leukocytes can also be detected using an antibody to the pathogenic protein aggregates. In one embodiment, the antibody is an anti-β-amyloid antibody such as 6E10, 4G8, AB5078P, 12F4, AB9234 or OMAB. AB9234 and OMAB are antibodies that bind to β-amyloid oligomers.

While the above methods contemplate detecting aggregates in intact, optionally permeabilized, cells, in another embodiment, aggregates are detected in lysed and/or frozen cells.

In some embodiments, the methods further comprise detecting additional proteins known to be associated with diseases associated with abnormal protein aggregation. For example hyperphosphorylated Tau, prion protein. alphaB-crystallin and alpha-synuclein are optionally detected. Optionally, anti-phospho-Tau is used to detect hyperphosphorylated Tau and 6H4 antibody is used to detect prion protein.

The present disclosure also provides kits for analyzing blood to detect a disease associated with abnormal protein aggregation.

In one embodiment, the kit comprises a probe that detects the presence of pathogenic protein aggregates in leukocytes as well as instructions for use.

In one embodiment, the instructions for use provide instructions on how to perform any of the methods described herein.

The probe is optionally a fluorescent probe that binds to the pathogenic protein aggregates. In another embodiment, the probe is a conformationally-sensitive fluorescent probe. Specific examples of conformationally-sensitive fluorescent probes useful for detecting amyloid peptides include, but are not limited to, Congo Red, Congo Red derivatives and bis-styrylbenzenes (e.g. K114, X34, BSB, FSB, IMSB, Chrysamine-G, methoxy-X34, methoxy-X04), thioflavin analogs (thioflavin-T, thioflavin-S, Pittsburgh compound B), thiazine red R, auramine-O and pentameric formyl thiophene acetic acid (p-FTAA) and related luminescent conjugated polythiophenes (LCPs) or luminescent conjugated oligothiophenes (LCOs).

In other embodiments, the probe is an antibody to pathogenic protein aggregates such as an anti β-amyloid antibody, for example, 6E10.

The kits are useful for analyzing blood to detecting various diseases associated with abnormal protein aggregation including, but not limited to, Alzheimer's disease, Parkinson's disease, Huntington's disease, mild cognitive impairment, cerebral amyloid angiopathy, myopathy, neuropathy, brain trauma, frontotemporal dementia, Pick's disease, multiple sclerosis, prion disorders and Down's syndrome.

The following non-limiting examples are illustrative of the present disclosure:

EXAMPLES

Example 1

Detection of Alzheimer's Disease from Blood Using Fluorescence Spectroscopy

Many neurological diseases such as AD, Parkinson's, Huntington's and prionopathies are associated with the misfolding and aggregation of proteins from their soluble functional state into highly ordered fibrillar assemblies with high β-sheet content. These pathologically unrelated disorders have in common specific binding to a classic amyloid probe, Congo Red, and are thus called "congophilic" diseases. Conformationally-sensitive fluorescent probes that specifically bind amyloid fibrils have been widely used for the investigation of protein aggregation (Styren at al 2000; Klunk et al 2002; Mathis at al 2002; Aslund et al 2009; Nilsson et al 2005; Hammarstrom at al 2010). Some newer probes have the additional property of detecting soluble oligomeric species, and altering their emission spectra depending on the protein aggregate they bind to, allowing them to identify minute deposits or subtle changes in conformation.

Advanced spectral imaging allows highly quantitative separation of spectra, including subtle variations from amyloid probes binding to different types of aggregates. Using these techniques, an assay was devised for the detection of misfolded proteins (Aβ or others) from brain and blood of an AD mouse model (Oakley at al 2006) and from human AD patients. Spectral signatures of protein aggregates labeled by probe X-34 (a Congo Red derivative) were studied from the CNS and blood.

Strong and specific signals were obtained from AD transgenic mouse brain plaques labeled with X-34, and it was possible to distinguish various states of "maturity" and aggregation within single senile plaques (FIG. 1). This strategy was also applied to human AD patient brains. Here, amyloid plaques could be distinguished from neurofibrillary tangles and autofluorescent lipofuscin in paraffin-embedded sections. β-amyloid signatures were very similar to those from AD mouse brain. Together, these results indicate that the method is capable of sensitive and potentially AD-specific detection of protein misfolding/aggregation.

Immunostaining AD transgenic mouse brain with an anti-Aβ antibody 6E10 showed that senile plaques with typical morphology of 6E10 immuno-positive (FIG. 2a). Further, 6E10-positive blood cells were also observed around a blood vessel (FIG. 2 *a* and *b*), showing that the cells ingested material that is very similar to that found in plaques. Without being bound by theory, it is believed that circulating leukocytes act as "sentinels" with the ability to carry misfolded proteins as a "memory" of their experience after trafficking through the diseased brain.

Whereas analyzing post-mortem brain is the de facto standard for AD diagnosis, it is highly impractical. A non-invasive technique was therefore sought. In support of the hypothesis that leukocytes act as "circulating sentinels", many such cells from AD mouse blood were strongly positive for X-34, with spectral signatures very similar to those from brain plaques, suggesting that it is possible to detect similar "AD-like pathology" in blood (FIG. 3*d*). The vast majority of these positive leukocytes were also immunopositive for Aβ (FIG. 3*a-c*), supporting the notion that they had trafficked into the AD brain, ingested then exported misfolded forms of Aβ. Probe signal from wild type (littermate control) leukocytes was negligible.

This method was then tested in human AD blood samples. Freshly isolated buffy coat from clinically diagnosed AD and control (healthy, stroke, Creutzfeldt-Jakob disease (CJD)) patients were subjected to a similar analysis. All AD samples showed strongly positive cells with X-34, exhibiting distinctive emission spectra, which were virtually absent from all controls (FIG. 4*a-b*). Strong AD-specific fluorescence signal was seen only in AD leukocytes (FIG. 4*c*). These results also show that CJD protein aggregates are not detectable using the probe X-34 with the basis spectra used for this analysis (specifically selected to detect AD), and show that different fluorescent probes and/or detection of different specific emission spectra, unique for CJD and not for AD, would be necessary to detect the unique putative misfolded proteins associated with CJD. Lastly, all X-34-positive leukocytes co-labeled with anti-Aβ (FIG. 5), indicating that as in AD mouse, it is possible to detect "AD-like pathology" in circulating human blood leukocytes.

Taken together, these observations show that it is possible to detect AD pathology in circulating leukocytes. Such peripheral abnormalities reflect relevant pathology in AD brain, and thus constitute a reliable test for AD.

Example 2

Detecting Protein Aggregates in Leukocytes Using Probe K114

Fluorescent probe K114, an amyloid-specific dye and an analogue of Congo Red, was used to detect protein aggregates in human leukocytes. In addition, fluorescence signals from the labeled leukocytes were processed using algorithms (for example, algorithms based on the Levenberg-Marquardt damped least-squares non-linear curve fitting algorithm) to separate disease-specific signals from background and auto fluorescence emission. A numerical score based on fluorescence emissions was calculated reflecting the probability that a test cell sample originated from a patient with a disease associated with abnormal protein aggregation.

Protocol

Blood was drawn from patients in an EDTA tube and placed on ice. The buffy coat (leukocytes) was isolated using standard techniques. Briefly, blood samples were centrifuged at 1,700 RCF at room temperature and the concentrated leukocyte band (middle white layer) was removed. Contaminating red blood cells were lysed by ACK lysing buffer for 3-5 min at room temperature and leukocyte samples were washed with PBS.

Leukocytes were fixed in a 10% neutralized buffered formalin. A small aliquot of fixed leukocytes were placed on a slide glass and dried. The dried sample was stained with fluorescent probe K114 or X-34.

The probe was washed with buffer, coverslipped with water-based mounting media and imaged on a laser scanning microscope.

Imaging was performed either with continuous-wave laser illumination (1-photon excitation with confocal detection) or with 2-photon excitation, both at various and multiple wavelengths.

Several images of several hundred cells each were acquired using a spectral imaging system that acquired 32 channels of spectrally-resolved data spanning 400-750 nm (typical).

Images of cells were analyzed for fluorescent inclusions (which are present in both control and AD/MCI (Mild Cognitive Impairment) samples). These were classified by size, and distinct fluorescent spectra extracted manually as an initial step. These "basis spectra" represent the various emitters in the sample: autofluorescence, laser backscatter artifact, several distinct emissions from each fluorescent probe. These spectra differ according to excitation wavelength, and are re-determined for each wavelength (typically 2 different excitation wavelengths were used).

Using these basis spectra, the combined fluorescence in the combined images was processed to determine the relative weighting/contribution of each basis spectrum for each sample, yielding a numerical coefficient for each basis spectrum. The software was based in part on the Levenberg-Marquardt damped least-squares non-linear curve fitting algorithm.

A ratio of coefficients was used to compute a "disease index" for each category: control, MCI (Mild Cognitive Impairment), AD, other neurological disorders. Different disorders e.g. CJD, BSE require different fluorescent probes and/or different basis spectra to detect unique putative misfolded proteins.

Results

AD-specific signals were observed in leukocytes from AD patients labeled with K114 (FIG. 6*a*). The emission spectra of healthy cells labeled with K114 were distinguishable with AD cells labeled with K114 (FIG. 6*b*).

FIG. 7 is a simplified composite index that reflects the probability that a subject has either AD or Mild Cognitive Impairment (MCI) ("ADR index" ie "AD related index"). Leukocytes were sampled from healthy controls (Healthy cent), stroke patients without AD/MCI (Stroke), patients with "other neurological disorders" (OND) and patients with Alzheimer's disease (AD), Mild Cognitive Impairment (MCI) and cerebral amyloid angiopathy (CAA). The OND patient had CJD.

While all the non-ADR controls (Healthy Control, Stroke and CJD) were negative, all of the ADR patients (AD+MCI) were positive. In addition, three out of four of the cerebral amyloid angiopathy (CAA) patients were positive. This data shows that the method clearly identifies patients with Alzheimer's disease and related disorders.

Example 3

Presence of Amyloids in the Brain of an MS Patient

It is generally believed that AD is a neurodegenerative disorder with secondary innate inflammation, but the thinking for multiple sclerosis (MS) is unclear. Initially, evidence was strong in favor of a primary autoimmune disorder with the resulting inflammatory assault driving demyelination and cortical atrophy. However, recent data from detailed pathological examination, and experience with potent anti-inflammatory therapies, cast doubt on this conclusion (Stys et al 2012).

Therefore, the possibility exists that MS may also be a primary degenerative disorder, with the unusually prominent inflammation a secondary response. What then might be at the root of MS? Pathology of later chronic MS (where the inflammatory reaction is less prominent) indicates that demyelinating lesions expand with time (possibly propagating from discrete foci within plaques?), and the prominent periventricular and cortical pathology suggests that some soluble factor (possibly circulating in the CSF?) may be responsible. Amyloids have this property in that they may propagate and misfold additional proteins, circulate as toxic soluble species (e.g. Aβ oligomers in AD), and later, condense into insoluble aggregates. FIG. 8 shows human MS brain stained with Congo Red, an amyloid probe. These data suggest that chronic MS plaques have deposits of amyloid. These deposits may be a primary feature of MS causing myelin and neuronal damage, as Aβ is thought to do in AD, or they may be reactive to chronic bouts of inflammation. Regardless, the presence of amyloid plaques in MS brain indicates that similar to AD, circulating leukocytes of MS patients are also likely to carry detectable amyloid aggregates.

Example 4

Larger Scale Study: Blood Test for AD Using Fluorescence Spectroscopy

Blood samples from 30 AD and 30 age-matched healthy controls, as well as other non-AD neurodegenerative disorders, were obtained. Buffy coat was isolated and leukocytes labeled with conformationally-sensitive probes. Spectral 2-photon and 1-photon images were acquired and fluorescence signals from leukocytes were processed using algorithms to separate AD-specific from background and autofluorescence emissions. The spectral signatures of the leukocyte amyloid probe fluorescence from AD subjects was virtually identical to that from human and mouse senile plaque, strongly suggesting that certain leukocyte subsets (≈1-2%) contain material that is similar to that found in cerebral plaques. Further, these probe-positive leukocytes co-label strongly for anti-Aβ antibody, consistent with the understanding certain leukocytes trafficked through the brain (microvasculature and/or parenchyma), were exposed to an Aβ-rich milieu, and brought with them a "memory" of this exposure that is detectable by the present methods. A numerical score based on the different fluorescence emissions was then calculated reflecting the probability that the sample originated from an AD patient. In select subjects, post-mortem neuropathological examination was performed to unequivocally confirm the diagnosis.

There is evidence that "activation" of leukocytes e.g. by infection, also increases probe fluorescence, though the spectral signatures differ. Therefore human subjects with various infections, auto-immune diseases, and lymphoproliferative disorders (leukemia, lymphoma) were also included to ensure the specificity of the method.

There is also evidence that 1-photon fluorescence excitation (confocal) can be used, greatly simplifying the technique and opening the way for future development of a relatively inexpensive high-throughput instrument, Example 5

Blood Test for Bovine Spongiform Encephalopathy (BSE) Using Fluorescence Spectroscopy Using blood from scrapie-infected and healthy mice, red blood cells (RBCs) were removed by osmotic shock, and non-RBC blood elements separated. Cells were stained with conformationally-sensitive amyloid probes. Strongly positive signal was only seen in scrapie blood elements, and no signal was found in uninfected mice. Moreover the spectral signature from the scrapie-infected blood samples was identical to scrapie spleen in proteinase K-resistant, anti-PrP-positive regions.

The method was then tested in experimental BSE samples. Frozen isolated buffy coat from neuropathologically proven BSE and non-BSE controls, together with healthy cows and those with other diseases (e.g. polio, brain abscess) were subjected to similar analysis using 2 different conformationally-sensitive amyloid probes, Both BSE samples were strongly positive, and all other samples (both healthy control and infected non-BSE cattle) were unequivocally negative. This data shows that the spectral fluorescence methods described herein are capable of reliably detecting markers in the blood present only in BSE-afflicted animals.

REFERENCES

1. Barnes, D. E. & Yaffe, K. The projected effect of risk factor reduction on Alzheimer's disease prevalence. *Lancet Neurol* 10, 819-828 (2011).
2. Selkoe, D. J. Alzheimer's disease: genes, proteins, and therapy. *Physiol Rev* 81, 741-766 (2001).
3. Britschgi, M. & Wyss-Coray, T. Systemic and acquired immune responses in Alzheimer's disease. *Int Rev Neurobiol* 82, 205-233 (2007).
4. de la Torre, J. C. Alzheimer disease as a vascular disorder: nosological evidence. *Stroke* 33, 1152-1162 (2002).
5. Deane, R. & Zlokovic, B. V. Role of the blood-brain barrier in the pathogenesis of Alzheimer's disease. *Curr Alzheimer Res* 4, 191-197 (2007).
6. Nagababu, E., Usatyuk, P. V., Enika, D., Natarajan, V. & Rifkind, J. M. Vascular endothelial barrier dysfunction mediated by amyloid-beta proteins. *J Alzheimers Dis* 17, 845-854 (2009).
7. Farkas, I. G. et al. Beta-amyloid peptide-induced blood-brain barrier disruption facilitates T-cell entry into the rat brain. *Acta Histochem* 105, 115 125 (2003).
8. Majumdar, A. at al. Degradation of fibrillar forms of Alzheimer's amyloid betapeptide by macrophages. *Neurobiol Aging* 29, 707-715 (2008).
9. Mildner, A. et al. Microglia in the adult brain arise from Ly-6ChiCCR2+ monocytes only under defined host conditions. *Nat Neurosci* 10, 1544-1553 (2007).
10. Simard, A. R., Soulet, D., Gowing, G., Julien, J. P. & Rivest, S. Bone marrowderived microglia play a critical role in restricting senile plaque formation in Alzheimer's disease. *Neuron* 49, 489-502 (2006).
11. Stamatovic, S. M. et al. Monocyte chemoattractant protein-1 regulation of bloodbrain barrier permeability. *J Cereb Blood Flow Metab* 25, 593-606 (2005).
12. McKhann, G. M. et al. The diagnosis of dementia due to Alzheimer's disease: recommendations from the National Institute on Aging-Alzheimer's Association workgroups on diagnostic guidelines for Alzheimer's disease. *Alzheimers Dement* 7, 263-269 (2011).
13. Styren, S. D., Hamilton, R. L., Styren, G. C. & Klunk, W. E. X-34, a fluorescent derivative of Congo red: a novel histochemical stain for Alzheimer's disease pathology. *J Histochem Cytochem* 48, 1223-1232 (2000).
14. Klunk, W. E. et al. Imaging Abeta plaques in living transgenic mice with multiphoton microscopy and methoxy-X04, a systemically administered Congo red derivative. *J Neuropathol Exp Neurol* 61, 797-805 (2002).
15. Mathis, C. A. et al. A lipophilic thioflavin-T derivative for positron emission tomography (PET) imaging of amyloid in brain. *Bioorg Med Chem Lett* 12, 295-298 (2002).
16. Aslund, A. et al. Novel pentameric thiophene derivatives for in vitro and in vivo optical imaging of a plethora of protein aggregates in cerebral amyloidoses. *ACS Chem Biol* 4, 673-684 (2009).
17. Nilsson, K. P., Herland, A., Hammarstrom, P. & Inganas, O. Conjugated polyelectrolytes: conformation-sensitive optical probes for detection of amyloid fibril formation. *Biochemistry* 44, 3718-3724 (2005).
18. Hammarstrom, P. et al. A fluorescent pentameric thiophene derivative detects in vitro-formed prefibrillar protein aggregates. *Biochemistry* 49, 6838-6845 (2010).
19. Oakley, H. et al. Intraneuronal beta-amyloid aggregates, neurodegeneration, and neuron loss in transgenic mice with five familial Alzheimer's disease mutations: potential factors in amyloid plaque formation. *J Neurosci* 26, 10129-10140 (2006).
20. Caumartin, J., Lemaoult, J. & Carosella, E. D. Intercellular exchanges of membrane patches (trogocytosis) highlight the next level of immune plasticity. *Transpl Immunol* 17, 20-22 (2006).
21. Thambisetty, M. & Lovestone, S. Blood-based biomarkers of Alzheimer's disease: challenging but feasible. *Biomark Med* 4, 65-79 (2010).
22. van Rossum, I. A. et al. Injury markers predict time to dementia in subjects with MCI and amyloid pathology. *Neurology* (2012).
23. Senanarong, V. et al. Alzheimer's disease dementia as the diagnosis best supported by the cerebrospinal fluid biomarkers: difference in cut-off levels from thai experience. *Int J Alzheimers Dis* 2012, 212063 (2012).
24. Jack, C. R. J. Alzheimer disease: new concepts on its neurobiology and the clinical role imaging will play. *Radiology* 263, 344-361 (2012).
25. Matsuda, H. & Imabayashi, E. Molecular neuroimaging in Alzheimer's disease. *Neuroimaging Clin N Am* 22, 57-65, viii (2012).
26. Nordstedt. C. et al. Human neutrophil phagocytic granules contain a truncated soluble form of the Alzheimer beta/A4 amyloid precursor protein (APP). *J Biol Chem* 269, 9805-9810 (1994).
27. Styren, S. D. et al. X-34, A Fluorescent Derivative of Congo Red: A Novel Histochemical Stain for Alzheimer's Disease Pathology. *J Histochem Cytochem September* 2000 vol. 48 no. 9 1223-1232
28. Crystal, A. S. et al. A comparison of amyloid fibrillogenesis using the novel fluorescent compound K114. *J Neurochem*. 2003 September; 86(6):1359-68.
29. Vicart, P. et al. A missense mutation in the alphaB-crystallin chaperone gene causes a desmin-related myopathy. *Nature Genetics* 20, 92-95 (1998)
30. Sharma M C, Goebel H H. Protein aggregate myopathies. *Neurol India*. 2005 September; 53(3):273-9.
31. Stys P K, et al. Will the real multiple sclerosis please stand up? *Nat Rev Neurosci*. 2012 July; 13(7):507-14.

We claim:
1. A method of determining whether a subject has a disease associated with abnormal protein aggregation or has an increased risk of developing a disease associated with abnormal protein aggregation, comprising:
   contacting leukocytes from the subject with a conformationally-sensitive fluorescent probe that binds directly to pathogenic protein aggregates,
   generating a fluorescence emission spectrum or an absorption spectrum of the probe bound to the pathogenic protein aggregates at a plurality of wavelengths, wherein the emission spectrum or the absorption spectrum of the conformationally-sensitive fluorescent probe changes when the probe is bound to the pathogenic protein aggregates, and
   comparing the fluorescence emission spectrum or absorption spectrum to one or more reference fluorescence emission spectra or reference absorption spectra representative of the probe contacted with reference leukocytes from a subject with a disease associated with abnormal protein aggregation,
   wherein correspondence between the fluorescence emission spectrum or absorption spectrum and the one or more reference fluorescence emission spectra or reference absorption spectra is indicative that the subject has a disease associated with abnormal protein aggregation or an increased risk of developing a disease associated with abnormal protein aggregation.
2. The method of claim 1 comprising:
   obtaining a blood sample from the subject;
   isolating leukocytes from the blood sample; and
   contacting the leukocytes with the probe that binds to pathogenic protein aggregates.
3. The method of claim 1 comprising:
   obtaining a blood sample from the subject;
   separating a buffy coat from the blood sample; and
   contacting the leukocytes of the buffy coat with the probe that binds to pathogenic protein aggregates.
4. The method of claim 1, wherein the probe is Congo Red, a Congo Red derivative, K114, X34, BSB, FSB, IMSB, Chrysamine-G, methoxy-X34, methoxy-X04, thioflavin-T, thioflavin-S, Pittsburgh compound B, thiazine red R, auramine-O, p-FTAA or a luminescent conjugated polythiophene (LCP) or luminescent conjugated oligothiophene (LCO) related to p-FTAA.
5. The method of claim 1, wherein the method comprises comparing the fluorescence emission spectrum or absorption spectrum of the probe contacted with the leukocytes to the fluorescence emission spectrum or absorption spectrum of the probe contacted with reference leukocytes from a reference subject who has a disease associated with abnormal protein aggregation.
6. The method of claim 1, wherein at least one reference emission spectrum or reference absorption spectrum is a fluorescent emission spectrum from reference leukocytes from a reference subject who has a disease associated with abnormal protein aggregation, and correspondence between the fluorescence emission spectrum and the at least one reference fluorescence emission spectrum indicates that the subject has a disease associated with abnormal protein aggregation.
7. The method of claim 1, wherein the method further comprises:
   performing spectral unmixing to determine the weightings of individual basis spectra that contribute to the fluorescence emission spectrum or absorption spectrum; and using the weightings to determine a probability that the subject has a disease associated with abnormal protein aggregation.

8. The method of claim 7, wherein the individual basis spectra are determined from samples of subjects known to have a disease associated with abnormal protein aggregation, samples of healthy control subjects and/or samples that have not been contacted with the probe.

9. The method of claim 7, wherein the spectral unmixing is performed using the Levenberg-Marquardt algorithm.

10. The method of claim 1, wherein the subject has or is suspected of having Alzheimer's disease, Parkinson's disease, Huntington's disease, mild cognitive impairment, cerebral amyloid angiopathy, myopathy, neuropathy, brain trauma, frontotemporal dementia, Pick's disease, multiple sclerosis, prion disorders or Down's syndrome.

11. The method of claim 1, wherein the pathogenic protein aggregates comprise β-amyloid, α-synuclein, huntingtin, tau protein, hyperphosphorylated tau protein (pTau), prion protein, αB-crystallin (CRYAB), desmin, selenoproteins, actin and/or myosin.

12. The method of claim 1, wherein the pathogenic protein aggregates comprise β-amyloids and the subject has or is suspected of having Alzheimer's disease.

13. The method of claim 1, wherein the probe is Congo Red, K114, X34, BSB, thioflavin-T or p-FTAA.

14. The method of claim 1, wherein the subject has or is suspected of having mild cognitive impairment or Alzheimer's disease.

* * * * *